US009876997B2

(12) United States Patent
Hanawa et al.

(10) Patent No.: US 9,876,997 B2
(45) Date of Patent: Jan. 23, 2018

(54) ENDOSCOPE

(71) Applicant: OLYMPUS CORPORATION, Tokyo (JP)

(72) Inventors: Takayuki Hanawa, Hachioji (JP); Shinji Yamashita, Tachikawa (JP); Yasunori Matsui, Hino (JP); Yuzuru Tanabe, Niza (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/493,774

(22) Filed: Apr. 21, 2017

(65) Prior Publication Data

US 2017/0230624 A1 Aug. 10, 2017

Related U.S. Application Data

(63) Continuation of application No. PCT/JP2016/057604, filed on Mar. 10, 2016.

(30) Foreign Application Priority Data

Mar. 30, 2015 (JP) ................. 2015-069762

(51) Int. Cl.
*A61B 1/00* (2006.01)
*H04N 9/04* (2006.01)
(Continued)

(52) U.S. Cl.
CPC ......... *H04N 9/045* (2013.01); *A61B 1/00186* (2013.01); *A61B 1/05* (2013.01);
(Continued)

(58) Field of Classification Search
CPC ................................................ A61B 1/00186
See application file for complete search history.

(56) References Cited

U.S. PATENT DOCUMENTS

2004/0263645 A1 12/2004 Okada et al.
2012/0092473 A1 4/2012 Takamatsu
(Continued)

FOREIGN PATENT DOCUMENTS

JP 2000-115790 A 4/2000
JP 2012-085715 A 5/2012
(Continued)

OTHER PUBLICATIONS

Japanese Office Action dated Nov. 1, 2016 received in Japanese Patent Application No. 2016-554753.
(Continued)

*Primary Examiner* — Mehrdad Dastouri
*Assistant Examiner* — Rowina Cattungal
(74) *Attorney, Agent, or Firm* — Scully, Scott, Murphy & Presser, P.C.

(57) ABSTRACT

An endoscope includes: an image sensor including: pixels for receiving light to generate image signals, and reading circuits sharing predetermined number of pixels with one another; a format converter configured to convert the image signals output from the image sensor into a predetermined format corresponding to a processing device for performing image processing on the image signals; and a connector including the format converter and configured to be connected to the processing device. The image sensor includes a color filter of a Bayer array in which a red filter for passing a red component and a first green filter for passing a green component are alternately arranged in even lines of horizontal lines of the pixels, and a second green filter for passing a green component and a blue filter for passing a blue component are alternately arranged in odd lines of the horizontal lines.

3 Claims, 8 Drawing Sheets

(51) Int. Cl.
    *A61B 1/05*     (2006.01)
    *H04N 5/378*    (2011.01)
    *H04N 5/363*    (2011.01)
    *H04N 9/64*     (2006.01)

(52) U.S. Cl.
    CPC ............. *H04N 5/363* (2013.01); *H04N 5/378* (2013.01); *H04N 9/64* (2013.01)

(56) References Cited

U.S. PATENT DOCUMENTS

2012/0327281 A1    12/2012    Mabuchi
2016/0255287 A1     9/2016    Mabuchi

FOREIGN PATENT DOCUMENTS

| JP | 2012-147163 A | 8/2012 |
| JP | 2013-005397 A | 1/2013 |
| JP | 2013-094269 A | 5/2013 |

OTHER PUBLICATIONS

International Search Report dated Jun. 14, 2016 issued in PCT/JP2016/057604.

(a) READING : $R_1 R_2 R_3 \cdots\cdots R_n G_{r1} G_{r2} G_{r3} \cdots\cdots G_{rn}$ (b) OUTPUT : $R_1 G_{r1} R_2 G_{r2} R_3 G_{r3} \cdots\cdots\cdots\cdots R_n G_{rn}$ (a) READING : $G_{b1} G_{b2} G_{b3} \cdots\cdots G_{bn} \cdots B_1 B_2 B_3 \cdots\cdots B_n$ (b) OUTPUT : $G_{b1} B_1 G_{b2} B_2 G_{b3} B_3 \cdots\cdots\cdots\cdots G_{bn} B_n$

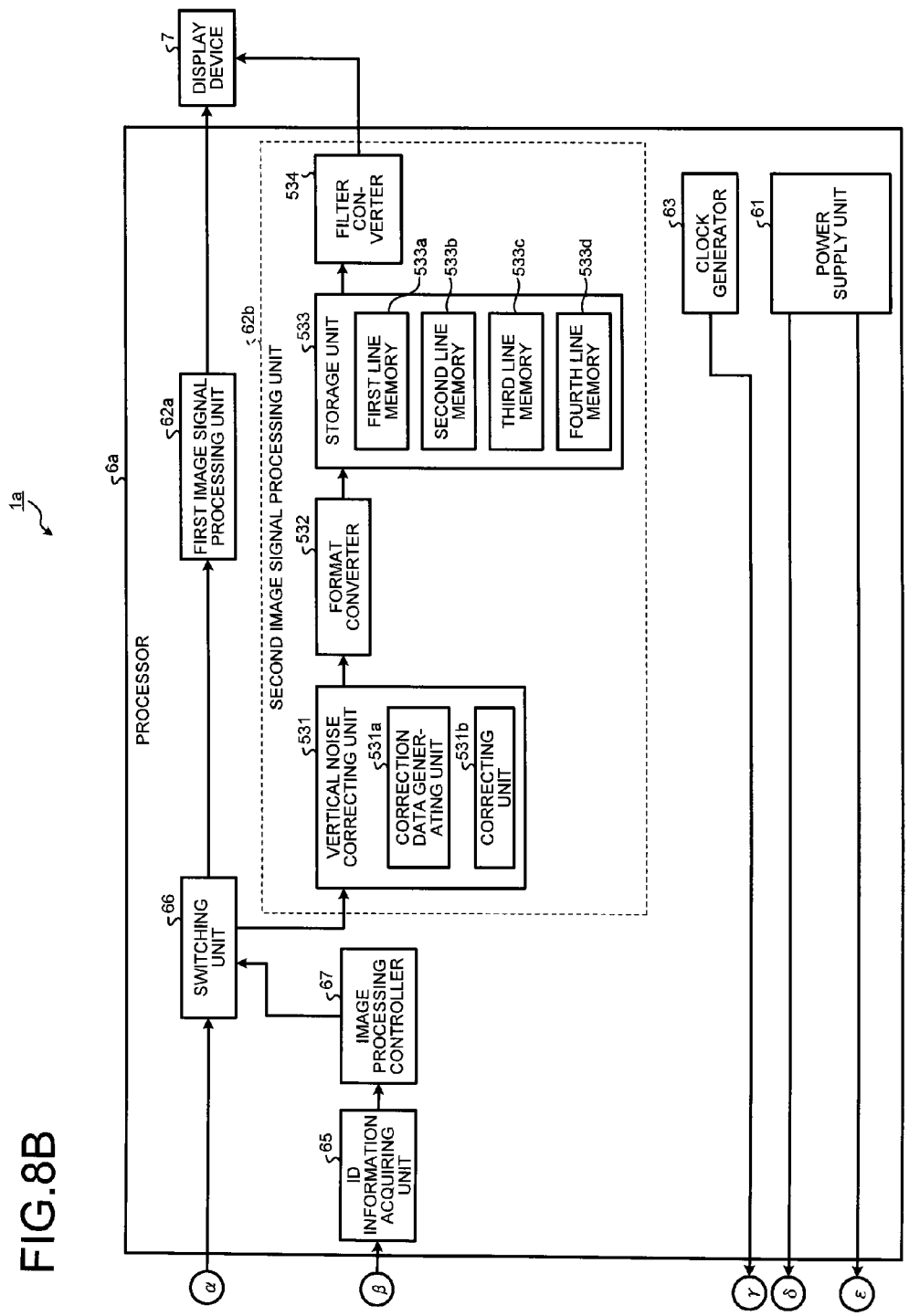

ENDOSCOPE

CROSS REFERENCES TO RELATED APPLICATIONS

This application is a continuation of PCT international application Ser. No. PCT/JP2016/057604 filed on Mar. 10, 2016 which designates the United States, incorporated herein by reference, and which claims the benefit of priority from Japanese Patent Application No. 2015-069762, filed on Mar. 30, 2015, incorporated herein by reference.

BACKGROUND

1. Technical Field

The disclosure relates to an endoscope configured to be introduced into a living body to capture in-vivo images.

2. Related Art

In recent years, there has been known a technology of generating an image signal of enhancing a contour of a subject in an imaging device such as an endoscope (see JP 2000-115790 A). According to this technology, the image signal of enhancing the contour of the subject is generated using a first synthesized signal obtained by alternately reading image signals from each of odd and even lines in a horizontal line of an image sensor provided with a color filter having a Bayer array at an exposure time and synthesizing the read image signals and a second synthesized signal obtained alternately reading image signals from each of the odd and even lines at a non-exposure time and synthesizing the read image signals.

SUMMARY

In some embodiments, an endoscope includes: an image sensor including: a plurality of pixels arranged two-dimensionally, the plurality of pixels being configured to receive external light to generate a plurality of image signals in accordance with a light receiving amount; and a plurality of reading circuits sharing predetermined number of pixels with one another and configured to read the plurality of image signals to transfer lines; a format converter configured to convert the plurality of image signals output from the image sensor into a predetermined format corresponding to a processing device for performing image processing on the plurality of image signals; and a connector including the format converter and configured to be connected to the processing device. The image sensor includes a color filter of a Bayer array in which a red filter for passing a red component and a first green filter for passing a green component are alternately arranged in even lines of horizontal lines of the plurality of pixels, and a second green filter for passing a green component and a blue filter for passing a blue component are alternately arranged in odd lines of the horizontal lines of the plurality of pixels. The plurality of reading circuits is configured to: read first image signals of the plurality of image signals from pixels corresponding to the red filter and read second image signals of the plurality of image signals from pixels corresponding to the first green filter in the even lines of the horizontal lines of the image sensor; and read third image signals of the plurality of image signals from pixels corresponding to the second green filter and read fourth image signals of the plurality of image signals from pixels corresponding to the blue filter in the odd lines of the horizontal lines of the image sensor. The format converter is configured to convert the plurality of image signals into an image format for the Bayer array by converting an arrangement in the color filter such that the first image signals and the second image signals are alternately arranged in the even lines of the image sensor read by the plurality of reading circuits, and the third image signals and the fourth image signals are alternately arranged in the odd lines of the image sensor read by the plurality of reading circuits.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIGS. 8A and 8B are block diagrams illustrating functions of main parts of an endoscope system according to a second embodiment of the present invention.

DETAILED DESCRIPTION

Figure 1:
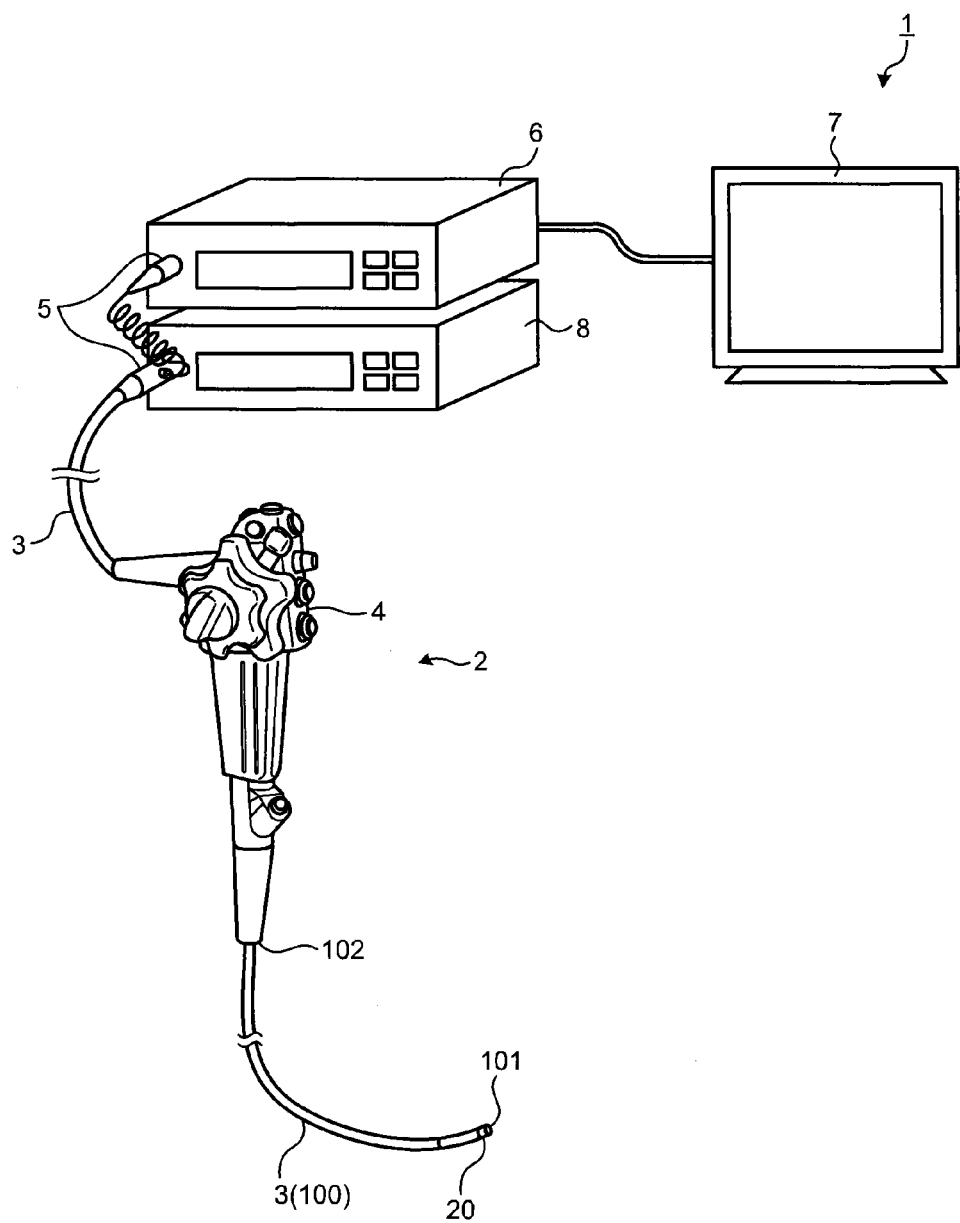
FIG. 1 is a diagram schematically illustrating an overall configuration of an endoscope system according to a first embodiment of the present invention.

Reference will be made below to exemplary embodiments of an endoscope system including an imaging device. The present invention is not limited to the embodiments. The same reference numerals are used to designate the same elements throughout the drawings. The drawings are schematic and the relation between the thickness and the width of each member and the ratio of each member, and the like are different from the reality. Also, parts having different dimensions and ratios are included in the drawings.

First Embodiment

Configuration of Endoscope System

FIG. 1 is a diagram schematically illustrating an overall configuration of an endoscope system according to a first embodiment of the present invention. An endoscope system 1 illustrated in FIG. 1 includes an endoscope 2, a transmission cable 3, a connector 5, a processor 6 (a processing device), a display device 7, and a light source 8.

The endoscope 2 includes an insertion portion 100 which is a part of the transmission cable 3 and which is configured to be inserted into a body cavity of a subject to capture an in-vivo image of the subject and output an image signal (image data) to the processor 6. The endoscope 2 includes an imaging unit 20 (an imaging device) configured to capture an in-vivo image on one end of the transmission cable 3, that is, a distal end 101 of the insertion portion 100 inserted into the body cavity of the subject. An operating unit 4 for receiving various operations of the endoscope 2 is connected to a proximal end 102 of the insertion portion 100. The imaging unit 20 is connected to the connector 5 by the transmission cable 3 through the operating unit 4. An image signal of an image captured by the imaging unit 20 is output to the connector 5 through the transmission cable 3, for example, having a length of several meters.

The connector 5 is configured to be connected to the processor 6 and the light source 8, performs predetermined signal processing on the image signals, performs analog-to-digital conversion (A/D conversion) on the image signals, and outputs the image signals to the processor 6.

The processor 6 includes a CPU (Central Processing Unit) or the like to perform predetermined image processing on the image signals output from the connector 5 and to perform overall control of the endoscope system 1. In the first embodiment, the processor 6 functions as a processing device.

The display device 7 displays an image corresponding to the image signals subjected to the image processing by the processor 6. The display device 7 displays various information relating to the endoscope system 1.

The light source 8 is configured as, for example, a halogen lamp or a white light emitting diode (LED) and irradiates the subject with illumination light from the distal end 101 of the insertion portion 100 of the endoscope 2 via the connector 5 and the transmission cable 3.

Figure 2:
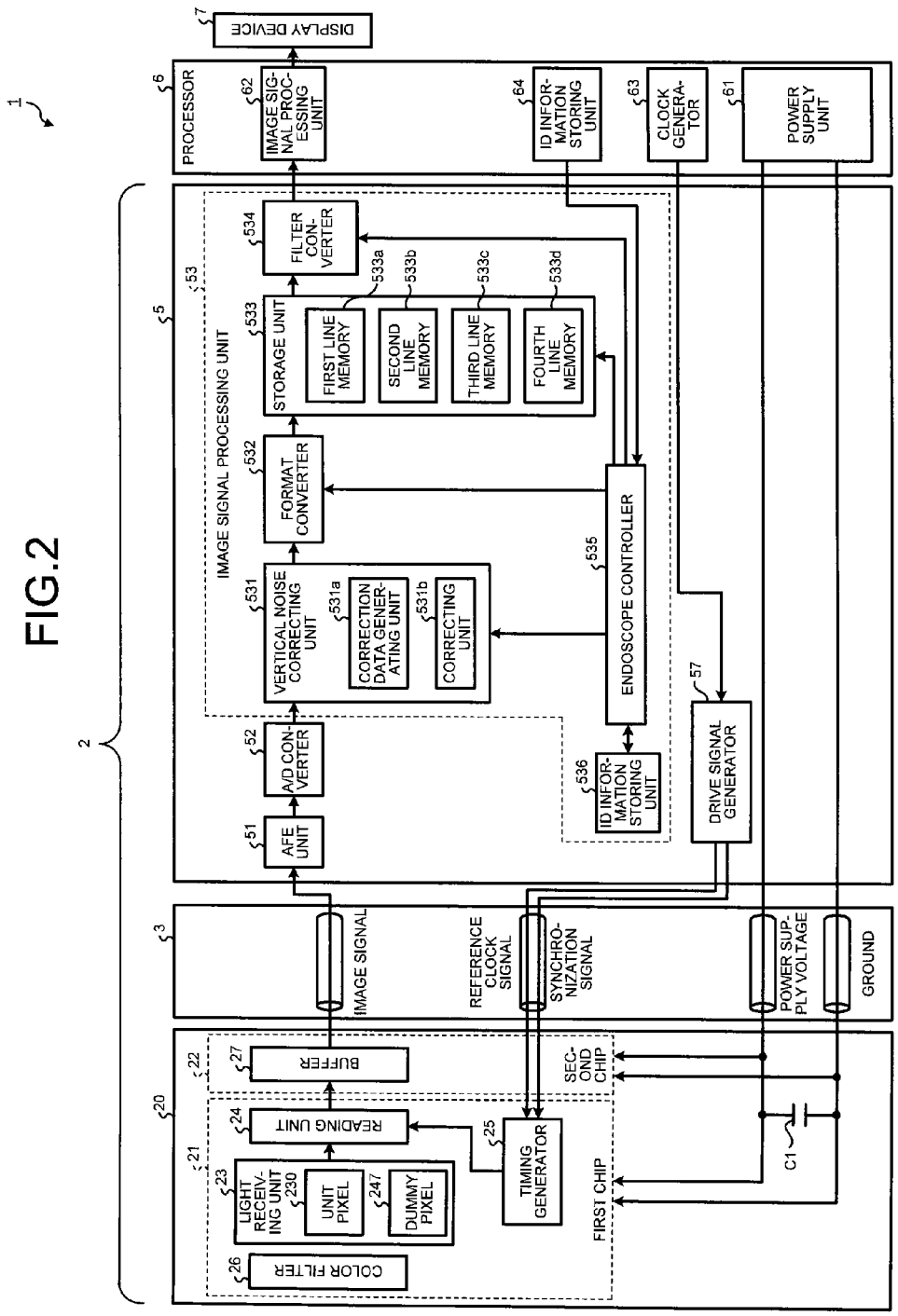
FIG. 2 is a block diagram illustrating functions of main parts of the endoscope system according to the first embodiment of the present invention.

FIG. 2 is a block diagram illustrating functions of main parts of the endoscope system 1. Referring to FIG. 2, a configuration of each element of the endoscope system 1 and an electric signal path inside the endoscope system 1 will be described in detail.

As illustrated in FIG. 2, the imaging unit 20 includes a first chip 21 (an image sensor) and a second chip 22.

The first chip 21 includes a light receiving unit 23, reading units 24 (reading circuits), a timing generator 25, and a color filter 26. The light receiving unit 23 includes a plurality of unit pixels 230 and a plurality of dummy pixels 247. The plurality of unit pixels 230 is arranged two-dimensionally in a matrix form, receives external light, and generates image signals in accordance with a light receiving amount, and outputs the image signals. The plurality of dummy pixels 247 is arranged for each transfer line (each vertical transfer line) of the plurality of unit pixels 230, and generates and outputs dummy signals used for correcting the image signals. The reading units 24 (reading circuits) share the light receiving unit 23 with one another for each predetermined unit pixel 230 and share predetermined number of pixels with one another, and read the dummy signals and the image signals obtained by photoelectric conversion in the light receiving unit 23. The timing generator 25 generates a timing signal based on a reference clock signal and a synchronization signal input from the connector 5 and outputs the timing signal to the reading unit 24. The color filter 26 is provided on a light receiving surface of each of the plurality of unit pixels 230. A detail configuration of the first chip 21 will be described with reference to FIG. 4.

Figure 3:
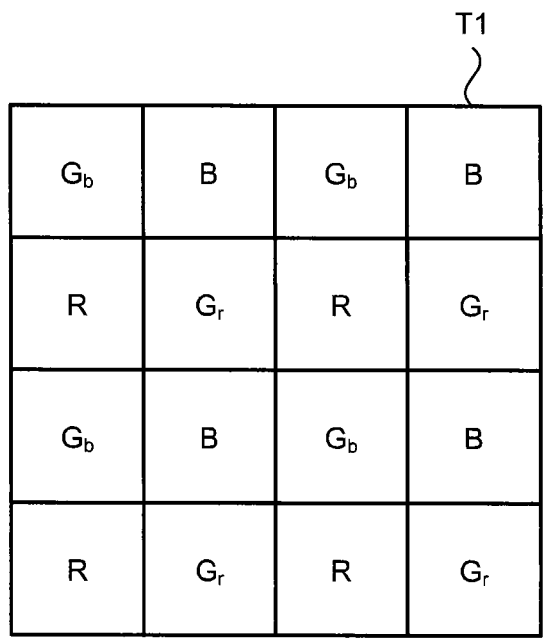
FIG. 3 is a schematic diagram illustrating a configuration of a color filter.

As illustrated in FIG. 3, the color filter 26 is realized by a Bayer filter T1 ($RG_rBG_b$) having a Bayer array including a red filter (hereinafter, referred to as a "R-filter") for passing a red light component, a first green filter (hereinafter, referred to as a "$G_r$-filter") for passing a green light component, a second green filter (hereinafter, referred to as a "$G_b$-filter") for passing a green light component, and a blue filter (hereinafter, referred to as a "B-filter") for passing a blue light component. The R-filter, the $G_r$-filter, the B-filter, and the $G_b$-filter are arranged at each unit pixel 230. Specifically, the color filter 26 has a configuration in which the R-filter and the $G_r$-filter are alternately disposed in this order on the even lines of the light receiving unit 23 and the $G_b$-filter and the B-filter are alternately disposed in this order on the odd lines of the light receiving unit 23.

The second chip 22 includes a buffer 27 which serves as a transmitter for transmitting an image signal output from the first chip 21 to the processor 6 via the transmission cable 3 and the connector 5. A combination of circuits mounted on the first chip 21 and the second chip 22 can be appropriately changed according to the convenience of setting.

The imaging unit 20 receives a power supply voltage VDD generated by a power supply unit 61 inside the processor 6 via the transmission cable 3 together with a ground GND. A power stabilizing capacitor C1 is provided between the power supply voltage VDD and the ground GND supplied to the imaging unit 20.

The connector 5 is provided with an analog front-end unit 51 (hereinafter, referred to as an "AFE unit 51"), an A/D converter 52, an image signal processing unit 53, and a drive signal generator 57. The connector 5 is connected to the processor 6, electrically connects the endoscope 2 (the imaging unit 20) and the processor 6 to each other, and serves as a relay processing unit relaying an electric signal. The connector 5 and the imaging unit 20 are connected to each other by the transmission cable 3 and the connector 5 and the processor 6 are connected to each other by, for example, a coil cable. The connector 5 is also connected to the light source 8.

The AFE unit 51 receives the image signal transferred from the imaging unit 20, performs an impedance matching process on the image signal by a passive element such as a resistor, extracts an AC component by a capacitor, and determines an operation point by a voltage dividing resistor. Subsequently, the AFE unit 51 corrects the image signal (the analog signal) and outputs the image signal to the A/D converter 52.

The A/D converter 52 converts the analog image signal input from the AFE unit 51 into a digital image signal and outputs the digital image signal to the image signal processing unit 53.

The image signal processing unit 53 includes, for example, a field programmable gate array (FPGA) and generates a reference clock signal (for example, a clock of 27 MHz) indicating a reference of an operation of each component of the endoscope 2 and a synchronization signal indicating a start position of each frame and performs a predetermined signal process such as a noise eliminating process, a format converting process, and a filter changing process on the digital image signal input from the A/D converter 52 while supplying the signals to the timing generator 25.

Here, a detailed configuration of the image signal processing unit 53 will be described. The image signal processing unit 53 includes at least a vertical noise correcting unit 531, a format converter 532, a storage unit 533, a filter converter 534, an endoscope controller 535, and an ID information storing unit 536.

The vertical noise correcting unit 531 corrects a vertical noise occurring in the image signal input via the A/D converter 52. Specifically, the vertical noise correcting unit 531 includes a correction data generating unit 531a which calculates a statistical value in each transfer line (each vertical transfer line to be described later) of the dummy signal output value included in a predetermined range and output from the dummy pixel 247 a plurality of times and generates correction data for correcting the image signal output from the unit pixel 230 based on the calculation result in each transfer line and a correcting unit 531b which corrects the image signal by subtracting the correction data of the corresponding transfer line from the image signal output from the unit pixel 230 in each transfer line based on the correction data of each transfer line generated by the correction data generating unit 531a and outputs the corrected image signal to the format converter 532. Here, the statistical value is one of an average value, a median value, and a mode in each transfer line of the dummy signal output value within a predetermined range (a normal value). The correction data generating unit 531a may generate correction data for the dummy signal output value within the predetermined range in each frame in which each of the plurality of unit pixels 230 generates the image signal.

The format converter 532 outputs the image signal output from the first chip 21 by converting the image signal into a predetermined format corresponding to the processor 6 connected thereto. Specifically, the format converter 532 performs a format converting process so that the format of the image signal input from the vertical noise correcting unit 531 after the correction of the vertical noise is converted into an array of a Bayer image. More specifically, the format converter 532 converts the format of the image signal into the image format of the Bayer array by converting the arrangement so that a plurality of image signals read from the pixels corresponding to the R-filters and a plurality of image signals read from the pixels corresponding to the $G_r$-filters for the horizontal signal of one line of the even lines of the light receiving unit 23 read by the reading unit 24 are alternately arranged and by converting the arrangement so that a plurality of image signals read from the pixels corresponding to the B-filters and a plurality of image signals read from the pixels corresponding to the $G_b$-filters for the horizontal signal of one line of the odd lines of the light receiving unit 23 read by the reading unit 24 are alternately arranged. For example, the format converter 532 converts the format of the image signal into the format of the image of the Bayer array by arranging a plurality of image signals read from the pixels corresponding to the R-filters in the odd vertical lines (2m+1, 2n) and arranging a plurality of image signals read from the pixels corresponding to the $G_r$-filters in the even vertical lines (2m, 2n) for the horizontal signal of one line of the even lines of the light receiving unit 23 read by the reading unit 24 and arranging a plurality of image signals read from the pixels corresponding to the $G_b$-filters in the odd vertical lines (2m+1, 2n+1) and arranging a plurality of image signals read from the pixels corresponding to the B-filters in the even vertical lines (2m, 2n+1) for the horizontal signal of one line of the odd lines of the light receiving unit 23 read by the reading unit 24.

The storage unit 533 includes a first line memory 533a which stores the image signal of the R-filter of which the format is converted into the array of the Bayer image by the format converter 532, a second line memory 533b which stores the image signal of the $G_r$-filter, a third line memory 533c which stores the image signal of the B-filter, and a fourth line memory 533d which stores the image signal of the $G_b$-filter.

The filter converter 534 converts the format of the filter of the image signal under the control of the endoscope controller 535. Specifically, the filter converter 534 converts the image signal of the Bayer filter into an image signal of a complementary color filter under the control of the endoscope controller 535.

The endoscope controller 535 controls elements constituting the image signal processing unit 53. The endoscope controller 535 acquires ID information of the processor 6 from an ID information storing unit 64 of the processor 6 and controls each element based on the acquired information. The endoscope controller 535 serves as an acquisition unit according to the first embodiment. A method of acquiring information necessary to control each element is not limited to the method using the above-mentioned ID information storing unit 64 and a voltage level of a connector pin (not illustrated) or a combination thereof may be used as the ID information.

The ID information storing unit 536 stores identification information indicating the type of the endoscope 2, the type of the first chip 21 (for example, the information of the color filter 26 or the shared pixel system), and the information of the format and the date of the image signal to be output.

The drive signal generator 57 generates the synchronization signal indicating the start position of each frame based on the reference clock signal (for example, the clock signal of 27 MHz) supplied from the processor 6 and used as a reference of the operation of each of the components of the endoscope 2 and outputs the synchronization signal to the timing generator 25 of the imaging unit 20 via the transmission cable 3 along with the reference clock signal. Here, the synchronization signal which is generated by the drive signal generator 57 includes a horizontal synchronization signal and a vertical synchronization signal.

The processor 6 is a control device for performing overall control of the endoscope system 1. The processor 6 includes the power supply unit 61, an image signal processing unit 62, a clock generator 63, and the ID information storing unit 64.

The power supply unit 61 generates a power supply voltage VDD and supplies the generated power supply voltage VDD to the imaging unit 20 via the connector 5 and the transmission cable 3 along with a ground GND.

The image signal processing unit 62 performs image processing such as a synchronizing process, a white balance (WB) adjusting process, a gain adjusting process, a gamma correcting process, a digital-to-analog (D/A) converting process, and a format converting process on the digital image signal subjected to the signal process in the image signal processing unit 53 so that the digital image signal is converted into the image signal and outputs the image signal to the display device 7.

The clock generator 63 outputs the reference clock signal to the drive signal generator 57.

The ID information storing unit 64 stores identification information indicating types of the processor 6, type information indicating types of a color filter that is compatible with the image signal processing unit 62, format information that is compatible with the image signal processing unit 62, and ID information recording a model year.

The display device 7 displays an image captured by the imaging unit 20 based on the image signal input from the image signal processing unit 62. The display device 7 is configured by using a display panel such as a liquid crystal or an organic EL (Electro Luminescence).

Configuration of First Chip

Figure 4:
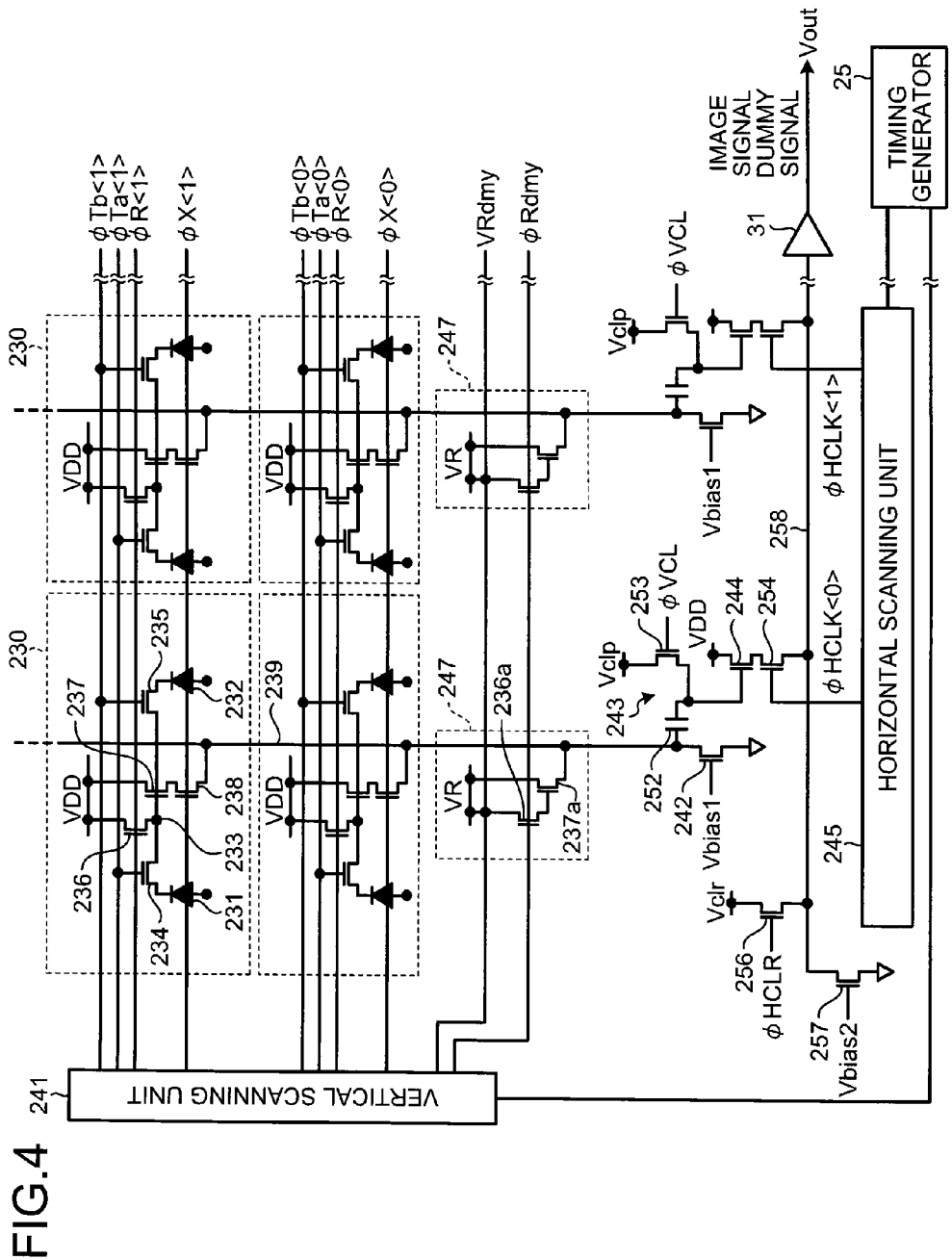
FIG. 4 is a circuit diagram illustrating a configuration of a first chip.

Next, a detailed configuration of the above-mentioned first chip 21 will be described. FIG. 4 is a circuit diagram illustrating a configuration of the first chip 21.

As illustrated in FIG. 4, the first chip 21 includes the timing generator 25, an output unit 31 (an amplifier), a vertical scanning unit 241 (a row selecting circuit), a constant current source 242, a noise eliminating unit 243 (a noise eliminating circuit), a column source follower transistor 244, and a horizontal scanning unit 245.

The timing generator 25 generates various drive signals based on the reference clock signal and the synchronization signal and outputs the drive signals to the vertical scanning unit 241 (the row selecting circuit), the noise eliminating unit 243, and the horizontal scanning unit 245 of the reading unit 24 to be described later, respectively.

The vertical scanning unit 241 drives each of the unit pixels 230 of the light receiving unit 23 using the constant current source 242 by applying row selection pulses φT <M> and φR <M> to the selected rows <M> (M=0, 1, 2 ..., m−1, m) of the light receiving unit 23 based on the drive signals (φT and φR) input from the timing generator 25, the image signal and the pixel resetting noise signal are transferred to a vertical transfer line 239 and are output to the noise eliminating unit 243. In the first embodiment, the vertical scanning unit 241 serves as a reading circuit and shares and reads the image signals from two unit pixels 230. In the first embodiment, the vertical transfer line 239 serves as a transfer line.

The noise eliminating unit 243 eliminates the pixel resetting noise signal and the output variation of each of the unit pixels 230 and outputs an image signal which is photoelectrically converted in each of the unit pixels 230. The noise eliminating unit 243 will be described in detail later.

The horizontal scanning unit 245 applies a column selection signal φHCLK <N> to the selected column <N> (N=0, 1, 2 ..., n−1, n) of the light receiving unit 23 based on the drive signal (φHCLK) supplied from the timing generator 25 so that the image signal photoelectrically converted in each of the unit pixels 230 is transferred and output to a horizontal transfer line 258 (the second transfer line) via the noise eliminating unit 243. In the first embodiment, the horizontal transfer line 258 serves as a transfer part configured to transmit the image signal output from each of the unit pixels 230.

The plurality of unit pixels 230 is arranged in a two-dimensional matrix form in the light receiving unit 23 of the first chip 21. Each of the unit pixels 230 includes a photoelectric conversion element 231 (a photodiode), a photoelectric conversion element 232, a charge converter 233, a transfer transistor 234 (a first transfer part), a transfer transistor 235, a charge converter resetting unit 236 (a transistor), a pixel source follower transistor 237, a pixel output switch 238 (a signal output unit), and the dummy pixel 247 (the reference signal generating unit). In the specification, the transfer transistor for transferring the signal charge from one or the plurality of photoelectric conversion elements and each of the photoelectric conversion elements to the charge converter 233 is referred to as a unit cell. That is, the unit cell includes one or the plurality of photoelectric conversion elements and a pair of transfer transistors and one unit cell is included in each of the unit pixels 230.

The photoelectric conversion element 231 and the photoelectric conversion element 232 photoelectrically convert incident light into a signal charge amount in response to the light amount and store the signal charge amount. Cathodes of the photoelectric conversion element 231 and the photoelectric conversion element 232 are respectively connected to one ends of the transfer transistor 234 and the transfer transistor 235 and anodes thereof are connected to the ground GND. The charge converter 233 is configured as a floating diffusion capacitor (FD) and converts a charge stored in the photoelectric conversion element 231 and the photoelectric conversion element 232 into a voltage.

The transfer transistor 234 and the transfer transistor 235 respectively transfer a charge from the photoelectric conversion element 231 and the photoelectric conversion element 232 to the charge converter 233. Each of the gates of the transfer transistor 234 and the transfer transistor 235 is connected to signal lines to which the drive pulses (the row selection pulses) φTa and φTb are supplied and the other ends thereof are connected to the charge converter 233. When the drive pulses φTa and φTb are supplied from the vertical scanning unit 241 via the signal line, the transfer transistor 234 and the transfer transistor 235 are turned on so that the signal charge is transferred from the photoelectric conversion element 231 and the photoelectric conversion element 232 to the charge converter 233.

The charge converter resetting unit 236 resets the charge converter 233 to a predetermined potential. In the charge converter resetting unit 236, one end is connected to the power supply voltage VDD, the other end is connected to the charge converter 233, and the gate is connected to the signal line to which the drive pulse φR is supplied. When the drive pulse OR is supplied from the vertical scanning unit 241 via the signal line, the charge converter resetting unit 236 is turned on so that the signal charge stored in the charge converter 233 is discharged and the charge converter 233 is reset to a predetermined potential.

In the pixel source follower transistor 237, one end is connected to the power supply voltage VDD, the other end is connected to one end of the pixel output switch 238, and the gate receives a signal (an image signal or a resetting signal) converted into a voltage by the charge converter 233.

The pixel output switch 238 outputs the signal converted into a voltage by the charge converter 233 to the vertical transfer line 239. In the pixel output switch 238, the other end is connected to the vertical transfer line 239 and the gate is connected to the signal line to which the drive pulse φX is supplied. When the drive pulse φX is supplied from the vertical scanning unit 241 to the gate of the pixel output switch 238 via the signal line, the pixel output switch 238 is turned on so that the image signal or the resetting signal is transferred to the vertical transfer line 239.

The dummy pixel 247 is provided in each transfer line of the unit pixel 230. The dummy pixel 247 includes a pixel resetting unit 236a and a pixel source follower transistor 237a. That is, in this configuration, the photoelectric conversion element 231 (the photodiode), the charge converter 233, and the transfer transistor 234 (the first transfer part) are omitted from the unit pixel 230.

The pixel resetting unit 236a fixes the gate of the pixel source follower transistor 237a to a predetermined potential. In the pixel resetting unit 236a, one end is connected to a power supply voltage VR, the other end is connected to the gate of the pixel source follower transistor 237a, and the gate is connected to the signal line to which the drive signal φRdmy is supplied.

When the drive signal φRdmy is supplied from the timing generator 25 to the gate of the pixel resetting unit 236a via the signal line, the pixel resetting unit 236a is turned on so that the gate of the pixel source follower transistor 237a is fixed to a predetermined potential (VRdmy).

In the pixel source follower transistor 237a, one end is connected to the power supply voltage VR supplied from a reference voltage generating unit (not illustrated), the other end is connected to the vertical transfer line 239, and the gate receives a predetermined potential (VRdmy). In the pixel source follower transistor 237a with such a configuration, when a selection operation to be described later is performed, the dummy signal (the column reference signal) corresponding to the predetermined potential VRdmy is transmitted to the vertical transfer line 239 via the pixel source follower transistor 237a.

Similarly to the normal unit pixel 230, in the first embodiment, if the drive signal φRdmy is supplied to the gate of the pixel resetting unit 236a when the power supply voltage VR is at the level of the power supply voltage VDD (for example, 3.3 V) and VRdmy (for example, 2 V) is input, the pixel source follower transistor 237a is turned on so that the dummy pixel 247 including the pixel resetting unit 236a is selected (a selection operation). If the drive signal φRdmy is supplied to the gate of the pixel resetting unit 236a when the power supply voltage VR is at the level of the non-selection voltage (for example, 1V) or VRdmy (for example, 1 V), the pixel source follower transistor 237a is turned off so that the selection of the dummy pixel 247 including the pixel resetting unit 236a is released (a non-selection operation).

In the constant current source 242, one end is connected to the vertical transfer line 239, the other end is connected to the ground GND, and the gate receives a bias voltage Vbias1. The constant current source 242 drives the unit pixel 230 by the constant current source 242 so that the output of the unit pixel 230 is read to the vertical transfer line 239. The signal read to the vertical transfer line 239 is input to the noise eliminating unit 243.

The noise eliminating unit 243 includes a transfer capacitor 252 (AC coupling capacitor) and a clamp switch 253 (a transistor).

In the transfer capacitor 252, one end is connected to the vertical transfer line 239 and the other end is connected to the column source follower transistor 244.

One end of the clamp switch 253 is connected to the signal line to which a clamp voltage Vclp is supplied from the reference voltage generating unit (not illustrated). In the clamp switch 253, the other end is connected between the transfer capacitor 252 and the column source follower transistor 244 and the gate receives a drive signal φVCL from the timing generator 25. The image signal which is input to the noise eliminating unit 243 is an optical noise signal including a noise component.

When the drive signal φVCL is input from the timing generator 25 to the gate of the clamp switch 253, the clamp switch 253 is turned on, so that the transfer capacitor 252 is reset by the clamp voltage Vclp supplied from the reference voltage generating unit (not illustrated). The image signal of which the noise is eliminated by the noise eliminating unit 243 is input to the gate of the column source follower transistor 244.

Since the noise eliminating unit 243 with such a configuration does not need the sampling capacitor, the capacitance of the transfer capacitor (AC coupling capacitor) 252 may be a capacitance which is enough for the input capacitance of the column source follower transistor 244. The noise eliminating unit 243 can decrease an occupied area in the first chip 21 by the absence of the sampling capacitor.

In the column source follower transistor 244, one end is connected to the power supply voltage VDD, the other end is connected to one end of a column selection switch 254 (a second transfer part), and the gate receives the image signal from which noise is eliminated by the noise eliminating unit 243.

In the column selection switch 254, one end is connected to the other end of the column source follower transistor 244, the other end is connected to the horizontal transfer line 258 (the second transfer line), and the gate is connected to the signal line to which the drive signal φHCLK <M> is supplied from the horizontal scanning unit 245. When the drive signal φHCLK <M> is supplied from the horizontal scanning unit 245 to the gate of the column selection switch 254 of the column <M>, the column selection switch 254 is turned on so that the signal of the vertical transfer line 239 of the column <M> (the image signal from which noise is eliminated by the noise eliminating unit 243) is transferred to the horizontal transfer line 258.

In a horizontal reset transistor 256, one end is connected to the ground GND, the other end is connected to the horizontal transfer line 258, and the gate receives a drive signal φHCLR from the timing generator 25. When the drive signal φHCLR is input from the timing generator 25 to the gate of the horizontal reset transistor 256, the horizontal reset transistor 256 is turned on so that the horizontal transfer line 258 is reset.

In a constant current source 257, one end is connected to the horizontal transfer line 258, the other end is connected to the ground GND, and a bias voltage Vbias2 is applied to the gate. The constant current source 257 reads the image signal from the vertical transfer line 239 to the horizontal transfer line 258. The image signal or the dummy signal which is read to the horizontal transfer line 258 is input to the output unit 31.

The output unit 31 amplifies the image signal and the dummy signal (the reference signal which is used as a reference when the transfer line is corrected) from which noise is eliminated if necessary and outputs the amplified signal (Vout).

Format Converting Process

Figure 5:
FIG. 5 is a schematic diagram illustrating an outline of a format converting process which is performed on even lines of a light receiving unit by a format converter.
Figure 6:
FIG. 6 is a schematic diagram illustrating an outline of a format converting process which is performed on odd lines of the light receiving unit by the format converter.

Next, a format converting process which is performed by the format converter 532 will be described. FIG. 5 is a schematic diagram illustrating an outline of the format converting process which is performed on the even lines of the light receiving unit 23 by the format converter 532. FIG. 6 is a schematic diagram illustrating an outline of the format converting process which is performed on the odd lines of the light receiving unit 23 by the format converter 532. In (a) of FIG. 5 and (a) of FIG. 6, the exemplary image signal input after the correction of the vertical noise by the vertical noise correcting unit 531 is shown. In (b) of FIG. 5 and (b) of FIG. 6, the exemplary image signal after the conversion of the format by the format converter 532 is shown. In FIG. 5, the unit pixel 230 is formed such that the R-filter is disposed on the photoelectric conversion element 231 and the $G_r$-filter is disposed on the photoelectric conversion element 232. In FIG. 6, the unit pixel 230 is formed such that the $G_b$-filter is disposed on the photoelectric conversion element 231 and the B-filter is disposed on the photoelectric conversion element 232. In FIGS. 5 and 6, "n" indicates an integer.

First, a format converting process which is performed on the even lines of the light receiving unit 23 by the format converter 532 will be described. As illustrated in FIG. 5, the format converter 532 performs a format converting process in which the image signal input from the vertical noise correcting unit 531 after the correction of the vertical noise is converted into the array of the Bayer image. Specifically, the format converter 532 stores the image signals of all R-filters of the horizontal signal of one line of the even line (2n) of the light receiving unit 23 (the image sensor) in the first line memory 533a by arranging the image signals in the odd lines (2m+1, 2n) of the odd vertical lines and stores the image signals of all $G_r$-filters in the second line memory 533b by arranging the image signals in the even lines (2m, 2n) of the vertical lines. More specifically, as illustrated in (b) of FIG. 5, the format converter 532 converts the image signals into the Bayer image array so that the image signals ($R_1$ to $R_n$) of the R-filters and the image signals ($G_{r1}$ to $G_{rn}$) of the $G_r$-filters of the image signals input after the correction of the vertical noise using the vertical noise correcting unit 531 in the horizontal signal of one line of the even lines (2n) of the light receiving unit 23 (the image sensor) are alternately arranged ($R_1G_{r1}R_2G_{r2} \ldots R_nG_{rn}$) Subsequently, the format converter 532 stores the image signal converted into the Bayer array in the first line memory 533a and the second line memory 533b, respectively.

Next, a format converting process which is performed on the odd lines of the light receiving unit 23 by the format converter 532 will be described. As illustrated in FIG. 6, the format converter 532 stores the images signals of all B-filters of the horizontal signal of one line of the odd lines (2n+1) of the light receiving unit 23 (the image sensor) in the third line memory 533c by arranging the image signals in the odd lines (2m+1, 2n+1) of the vertical lines and stores the image signals of all $G_b$-filters in the fourth line memory 533d by arranging the image signals in the even lines (2m, 2n+1) of the vertical lines. More specifically, as illustrated in (b) of FIG. 6, the format converter 532 converts the image signals into the Bayer image array so that the image signals ($B_1$ to $B_n$) of the B-filters and the image signals ($G_{b1}$ to $G_{bn}$) of the $G_r$-filters of the image signals input after the correction of the vertical noise using the vertical noise correcting unit 531 in the horizontal signal of one line of the odd lines (2n+1) of the light receiving unit 23 (the image sensor) are alternately arranged ($G_{b1}B_1G_{b2}B_2 \ldots G_{bn}B_n$). Subsequently, the format converter 532 stores the image signal converted into the Bayer array in the third line memory 533c and the fourth line memory 533d, respectively.

In this way, the format converter 532 stores the image signals of all R-filters of the horizontal signals of one line of the even lines (2n) of the image signals input after the correction of the vertical noise using the vertical noise correcting unit 531 in the first line memory 533a by arranging the image signals in the odd lines (2m+1, 2n) of the vertical lines and stores the image signals of all $G_r$-filters in the second line memory 533b by arranging the image signals in the even lines (2m, 2n) of the vertical lines. At the same time, the format converter 532 stores the image signals of all B-filters of the horizontal signal of one line in the odd lines (2n+1) of the light receiving unit 23 (the image sensor) in the third line memory 533c by arranging the image signals in the odd lines (2m+1, 2n+1) of the vertical lines and stores the image signals of all $G_b$-filters in the fourth line memory 533d by arranging the image signals in the even lines (2m, 2n+1) of the vertical lines. Accordingly, the image signal of the first chip 21 read by the pixel sharing method can be converted into the Bayer format. As a result, since the image signal processing unit 62 corresponding to the pixel sharing method does not need to be provided in the processor 6, high user-friendliness and excellent versatility are obtained.

Converting Method of Filter Converter

Next, a converting method of the filter converter 534 will be described. The filter converter 534 acquires the image signal of the Bayer array from each of the first line memory 533a, the second line memory 533b, the third line memory 533c, and the fourth line memory 533d under the control of the endoscope controller 535, and converts the acquired image signal of the Bayer array into a color filter that is compatible with the processor 6. Specifically, the endoscope controller 535 causes the filter converter 534 to perform conversion into a filter that is compatible with the processor 6 based on types of the color filter compatible with the image signal processing unit 62 included in the ID information acquired from the ID information storing unit 64 of the processor 6. More specifically, as illustrated in FIG. 7, if the image signal processing unit 62 of the processor 6 is compatible with the complementary color filter, the filter converter 534 converts the image signal of the Bayer filter into the image signal of the complementary color filter and outputs the image signal to the image signal processing unit 62.

For example, the filter converter 534 generates the image signals of the complementary color of cyan (hereinafter, a "Cy-filter") and green (hereinafter, a "G-filter") in the odd lines forming the image and the image signals of the complementary color of yellow (hereinafter, a "Y-filter") and magenta (hereinafter, a "Mg-filter") in the even lines based on the image signal of the Bayer array acquired from each of the first line memory 533a, the second line memory 533b, the third line memory 533c, and the fourth line memory 533d.

Figure 7:
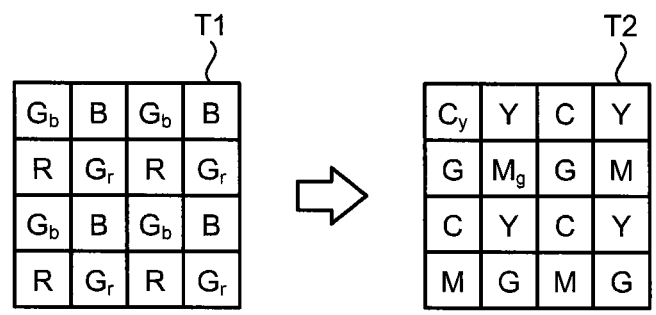
FIG. 7 is a schematic diagram illustrating a converting method of a filter converter.

Specifically, as illustrated in FIG. 7, the filter converter 534 converts the image signal of the Bayer filter T1 into the image signal of the complementary color filter T2 by calculating the image signal of the Cy-filter and the image signal of the G-filter of the complementary color filter using the image signal (the blue component) of the B-filter stored in the third line memory 533c and the image signal (the second green component) of the $G_b$-filter stored in the fourth line memory 533d. More specifically, the filter converter 534 calculates the image signal of the Cy-filter of the complementary color filter by adding the image signal of the B-filter stored in the third line memory 533c and the image signal of the $G_b$-filter stored in the fourth line memory 533d and calculates the image signal of the G-filter of the complementary color filter T2 by using the image signal of the $G_b$-filter stored in the fourth line memory 533d.

The filter converter 534 converts the image signal of the Bayer filter T1 into the image signal of the complementary color filter T2 by calculating the image signal (the magenta component) of the Mg-filter and the image signal (the yellow component) of the Y-filter of the complementary color filter using the image signal (the red component) of the R-filter stored in the first line memory 533a, the image signal (the first green component) of the $G_r$-filter stored in the second line memory 533b, and the image signal (the blue component) of the B-filter stored in the third line memory 533c.

Specifically, the filter converter 534 calculates the image signal of the Y-filter of the complementary color filter by adding the image signal of the R-filter stored in the first line memory 533a and the image signal of the $G_r$-filter stored in the second line memory 533b and calculates the image signal of the Mg-filter of the complementary color filter T2 by adding the image signal of the R-filter stored in the first line memory 533a, the image signal of the $G_r$-filter stored in the second line memory 533b, and the image signal of the B-filter stored in the third line memory 533c.

In this way, the filter converter 534 acquires the image signal of the Bayer array from each of the first line memory 533a, the second line memory 533b, the third line memory 533c, and the fourth line memory 533d under the control of the endoscope controller 535 and converts the acquired image signal of the Bayer array into the image signal of the color filter corresponding to the processor 6. When the image signal processing unit 62 of the processor 6 can correspond to the image signal of the Bayer filter, the filter converter 534 outputs the image signal to the processor 6 without converting the filter and converting the image signals of the color components of the first line memory 533a to the fourth line memory 533d. As a result, since the image signal processing unit 62 corresponding to the filter of the Bayer array may not be provided in the processor 6, high user-friendliness and excellent versatility are obtained.

According to the first embodiment, the format converter 532 stores the image signals of all R-filters of the horizontal signal of one line of the even lines (2n) of the image signals input after the correction of the vertical noise using the vertical noise correcting unit 531 in the first line memory 533*a* by arranging the image signals in the odd lines (2m+1, 2n) of the vertical lines and stores the image signals of all $G_r$-filters in the second line memory 533*b* by arranging the image signals in the even lines (2m, 2n) of the vertical lines. At the same time, the format converter 532 stores the image signals of all B-filters of the horizontal signal of one line of the odd lines (2n+1) in the third line memory 533*c* by arranging the image signals in the odd lines (2m+1, 2n+1) of the vertical lines and stores the image signals of all $G_b$-filters in the fourth line memory 533*d* by arranging the image signals in the even lines (2m, 2n+1) of the vertical lines. Accordingly, the image signal read by the pixel sharing method can be converted into the Bayer format. As a result, since the image signal processing unit 62 corresponding to the pixel sharing method may not be provided in the processor 6, high user-friendliness and excellent versatility are obtained.

Further, according to the first embodiment, the filter converter 534 acquires the image signal of the Bayer array from each of the first line memory 533*a*, the second line memory 533*b*, the third line memory 533*c*, and the fourth line memory 533*d* under the control of the endoscope controller 535 and converts the acquired image signal of the Bayer array into the filter corresponding to the processor 6. As a result, since the image signal of the Bayer filter is converted into the image signal of the complementary color filter even when the processor 6 can correspond to the image signal of the complementary color filter, high user-friendliness and excellent versatility are obtained.

Further, according to the first embodiment, since the format converter 532 converts the format of the image signal input from the vertical noise correcting unit 531 after the correction of the vertical noise, a high-quality image can be obtained.

Second Embodiment

Next, a second embodiment of the present invention will be described. In the above-described first embodiment, the endoscope 2 changes the content of the output image signal in response to the type of the processor 6, but in the second embodiment, the processor changes the content of the image process in response to the endoscope. The same reference numerals will be used to designate the same elements as those of the endoscope system 1 according to the first embodiment and the explanation thereof will be omitted.

Configuration of Endoscope System

Figure 8A:
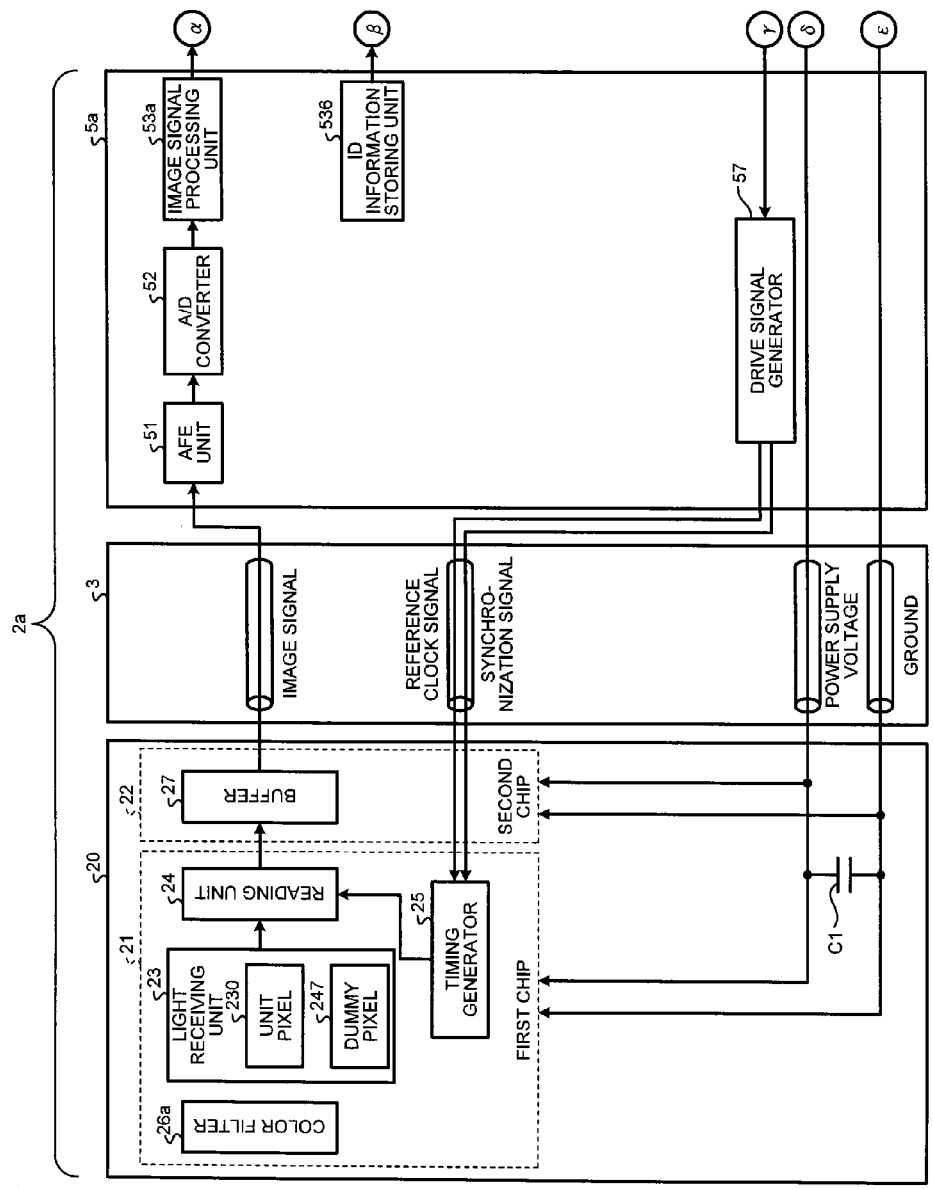

FIGS. 8A and 8B are block diagrams illustrating a function of a main part of an endoscope system according to the second embodiment of the present invention. As illustrated in FIGS. 8A and 8B, an endoscope system 1*a* includes an endoscope 2*a*, a processor 6*a*, and the display device 7.

Configuration of Endoscope

First, a configuration of the endoscope 2*a* will be described. The endoscope 2*a* includes a color filter 26*a* and a connector 5*a* instead of the color filter 26 of the first chip 21 and the connector 5 of the endoscope 2 according to the above-described first embodiment. The color filter 26*a* is configured as a complementary color filter (CyGYMg) (for example, the complementary color filter T2 of FIG. 7).

The connector 5*a* includes the AFE unit 51, the A/D converter 52, an image signal processing unit 53*a*, the ID information storing unit 536, and the drive signal generator 57.

The image signal processing unit 53*a* includes, for example, an FPGA, generates a reference clock signal (for example, a clock of 27 MHz) indicating a reference of an operation of each component of the endoscope 2*a* and a synchronization signal indicating a start position of each frame, and performs a predetermined signal process such as a noise eliminating process on the digital image signal input from the A/D converter 52 while supplying the signals to the timing generator 25.

Configuration of Processor

Next, a configuration of the processor 6*a* will be described. The processor 6*a* includes the power supply unit 61, a first image signal processing unit 62*a*, a second image signal processing unit 62*b*, the clock generator 63, an ID information acquiring unit 65, a switching unit 66, and an image processing controller 67.

The first image signal processing unit 62*a* performs image processing such as a synchronizing process, a white balance (WB) adjusting process, a gain adjusting process, a gamma correcting process, a digital-to-analog (D/A) converting process, and a format converting process on the digital image signal (the image signal of the complementary color filter) subjected to the signal process in the image signal processing unit 53*a* and input via the switching unit 66 so that the digital image signal is converted into the image signal and outputs the image signal to the display device 7.

The second image signal processing unit 62*b* performs image processing such as a format converting process, a filter converting process, a synchronizing process, a white balance (WB) adjusting process, a gain adjusting process, a gamma correcting process, and a digital-to-analog (D/A) converting process on the digital image signal (the image signal of the Bayer filter) subjected to the signal process in the image signal processing unit 53*a* and input via the switching unit 66 so that the digital image signal is converted into the image signal and outputs the image signal to the display device 7. The second image signal processing unit 62*b* includes at least the vertical noise correcting unit 531, the format converter 532, the storage unit 533, and the filter converter 534 according to the above-described first embodiment.

The ID information acquiring unit 65 acquires the ID information of the endoscope 2*a* from the ID information storing unit 536 of the endoscope 2*a* connected to the processor 6*a* and outputs the acquired ID information to the image processing controller 67.

Under the control of the image processing controller 67, the switching unit 66 switches an output destination of the image signal input from the endoscope 2*a* in response to the type of the endoscope 2*a* connected to the processor 6*a*.

The image processing controller 67 includes a CPU or the like and performs overall control of the operation of each component of the processor 6*a*. The image processing controller 67 controls the switching unit 66 based on the ID information input from the ID information acquiring unit 65 to switch an output destination of the image signal input from the endoscope 2*a*. Specifically, the image processing controller 67 switches the switching unit 66 so that the image signal input from the endoscope 2*a* is input to the first image signal processing unit 62*a* when the filter information of the endoscope 2*a* included in the ID information input from the ID information storing unit 536 is the complementary color filter and switches the switching unit 66 so that the image signal input from the endoscope 2a is input to the second image signal processing unit 62b when the filter information of the endoscope 2a included in the ID information input from the ID information acquiring unit 65 is the Bayer filter.

According to the second embodiment, the processor 6a includes two filters, that is, the first image signal processing unit 62a and the second image signal processing unit 62b respectively corresponding to the Bayer filter and the complementary color filter and the image processing controller 67 switches the output destination to which the image signal is output by the switching unit 66 to the first image signal processing unit 62a or the second image signal processing unit 62b based on the ID information of the endoscope 2a input from the ID information acquiring unit 65. Accordingly, since the image signal subjected to an image process corresponding to the endoscope 2a connected to the processor 6a can be output to the display device 7 even when different types of endoscopes 2a are connected to the processor 6a, versatility can be improved.

Other Embodiments

In the first and second embodiments, the image signal processing unit is provided in the connector, but may be provided in, for example, the operating unit of the endoscope.

According to some embodiments, it is possible to provide an endoscope which has high user-friendliness and excellent versatility.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
 an image sensor including:
  a plurality of pixels arranged two-dimensionally, the plurality of pixels being configured to receive external light to generate a plurality of image signals in accordance with a light receiving amount; and
  a plurality of reading circuits sharing predetermined number of pixels with one another and configured to read the plurality of image signals to transfer lines;
 a format converter configured to convert the plurality of image signals output from the image sensor into a predetermined format corresponding to a processing device for performing image processing on the plurality of image signals; and
 a connector including the format converter and configured to be connected to the processing device,
 wherein the image sensor includes a color filter of a Bayer array in which a red filter for passing a red component and a first green filter for passing a green component are alternately arranged in even lines of horizontal lines of the plurality of pixels, and a second green filter for passing a green component and a blue filter for passing a blue component are alternately arranged in odd lines of the horizontal lines of the plurality of pixels,
 wherein the plurality of reading circuits is configured to:
  read first image signals of the plurality of image signals from pixels corresponding to the red filter and read second image signals of the plurality of image signals from pixels corresponding to the first green filter in the even lines of the horizontal lines of the image sensor; and
  read third image signals of the plurality of image signals from pixels corresponding to the second green filter and read fourth image signals of the plurality of image signals from pixels corresponding to the blue filter in the odd lines of the horizontal lines of the image sensor, and
 wherein the format converter is configured to convert the plurality of image signals into an image format for the Bayer array by converting an arrangement in the color filter such that the first image signals and the second image signals are alternately arranged in the even lines of the image sensor read by the plurality of reading circuits, and the third image signals and the fourth image signals are alternately arranged in the odd lines of the image sensor read by the plurality of reading circuits.

2. The endoscope according to claim 1,
 wherein the image sensor includes a plurality of dummy pixels provided for each of the transfer lines in an arrangement of the plurality of pixels, the plurality of dummy pixels being configured to generate and output dummy signals to be used for correcting the plurality of image signals,
 wherein the endoscope further comprises:
  a correction data generating unit configured to calculate, for each of the transfer lines, a statistical value of output values of the dummy signals output a plurality of times from the plurality of dummy pixels, and generate, for each of the transfer lines, correction data for correcting the plurality of image signals based on the statistical value; and
  a correcting unit configured to correct the plurality of image signals based on the correction data generated by the correction data generating unit, and
 wherein the format converter is configured to convert the plurality of image signals corrected by the correcting unit into the predetermined format.

3. The endoscope according to claim 1, further comprising:
 an acquisition unit configured to acquire, from the processing device connected to the endoscope, identification information including type information indicating types of a color filter that is compatible with the processing device; and
 a filter converter configured to convert the plurality of image signals converted by the format converter into image signals of the color filter that is compatible with the processing device, based on the identification information acquired by the acquisition unit.

* * * * *